United States Patent [19]

Hobbs, Jr.

[11] Patent Number: 5,262,536

[45] Date of Patent: *Nov. 16, 1993

[54] REAGENTS FOR THE PREPARATION OF 5'-TAGGED OLIGONUCLEOTIDES

[75] Inventor: Frank W. Hobbs, Jr., Wilmington, Del.

[73] Assignee: E. I. Du Pont de Nemours and Company, Wilmington, Del.

[*] Notice: The portion of the term of this patent subsequent to Mar. 5, 2008 has been disclaimed.

[21] Appl. No.: 622,265

[22] Filed: Dec. 5, 1990

Related U.S. Application Data

[62] Division of Ser. No. 244,982, Sep. 15, 1988, Pat. No. 4,997,928.

[51] Int. Cl.$^5$ .................. C07D 311/02; C07D 311/82; C07F 9/24; C07F 9/06
[52] U.S. Cl. .................................... 546/25; 549/223; 549/283; 558/168; 558/191; 558/192; 558/218; 536/25.32
[58] Field of Search .................. 435/6; 536/27, 28, 29, 536/25.32; 558/93, 95, 168, 191, 192, 218; 549/385, 223, 283; 546/242, 25

[56] References Cited

U.S. PATENT DOCUMENTS

| | | | |
|---|---|---|---|
| 4,275,149 | 6/1981 | Litman et al. | 435/7 |
| 4,374,925 | 2/1983 | Litman et al. | 435/7 |
| 4,547,569 | 10/1985 | Letsinger | 536/25.32 |
| 4,739,044 | 4/1988 | Stabinsky | 536/25.3 |
| 4,757,141 | 7/1988 | Fung et al. | 536/25.32 |
| 4,797,480 | 1/1989 | Sorbi et al. | 536/26.13 |
| 4,873,355 | 10/1989 | Hobbs et al. | 558/61 |
| 4,965,349 | 10/1990 | Woo et al. | 536/25.3 |
| 4,997,928 | 3/1991 | Hobbs, Jr. | 536/27 |

FOREIGN PATENT DOCUMENTS

| | | |
|---|---|---|
| 202758 | 11/1986 | European Pat. Off. . |
| 252683 | 1/1988 | European Pat. Off. . |
| 305201 | 1/1989 | European Pat. Off. . |
| 0340605 | 11/1989 | European Pat. Off. . |
| 3446635 | 6/1985 | Fed. Rep. of Germany . |
| WO8912642 | 12/1989 | PCT Int'l Appl. . |

OTHER PUBLICATIONS

C. A. Stein, et al., "Phosphorothioate and Normal Oligodeoxyribonucleotides with 5'-linked acridine: Characterization and Preliminary Kinetics of Cellular Uptake" Gene 72, pp. 333–341 (1988).
Bannwarth et al. Tetrahedron Letters, vol. 30, No. 12, pp. 1513–1516, (1989).
Draper et al., Biochemistry, vol. 19, pp. 1774–1781 (1980).
Smith et al., Nature, vol. 321, pp. 674–679 (1986).
Smith et al., Nucl. Acids Res., vol. 13, pp. 2399–2412, (1985).
Ansorge et al., J. Biochem. Biophys. Methods, vol. 13, pp. 1315–1323 (1986).
Coull et al., Tetrahedron Letters, vol. 27, pp. 3991–3994 (1986).
Spraat et al., Nucl. Acids Res., vol. 15, pp. 6181–6196 (1987).
Tanaka et al. Tetrahedron Letters, vol. 28, pp. 2611–2614 (1987).
Connolly et al. Nucl. Acids Res. 15:3131–3139, 1987.
Agrawal et al., Nucleic Acids Res. 14:6227–6245 (1986).
Tanaka et al., Nucleic Acids Res. 15:6209–6224 (1987).
Sinha, et al., Nucleic Acids Res. 16:2659–2669 (1988).
Sproat et al., Nucleic Acids Res. 15:4837–4848 (1987).
Connolly et al., Nucleic Acids Res. 13:4485–4502 (1985).
Thuren et al., Clin. Chem. 31(5):714–717 (1985).
Kinnunen et al., Thin Solid Films 132:193–203 (1985).
Thuren et al., Chem. & Phys. Lipids 41:329–334 (1986).
Alexandrova et al., Bioorg. Khim. 31(5):643–647 (1987).
Sonveaux, Bioorg. Chem. 14:274–325 (1986).
S. Narang (Ed.), Synthesis and Applications of DNA and RNA, Academic Press (1987) pp. 18–34 and 47–79.
Garegg et al., Tet. Lett. 27:4051–4054 (1986).

*Primary Examiner*—Johnnie R. Brown
*Assistant Examiner*—Gary L. Kunz

[57] ABSTRACT

Fluorescent reagents possessing an activated phosphate for the convenient covalent coupling to the 5'-hydroxyl of oligonucleotides. A class of 5'-fluorescence-tagged oligonucleptides is also disclosed.

6 Claims, 2 Drawing Sheets

REAGENTS FOR THE PREPARATION OF 5'-TAGGED OLIGONUCLEOTIDES

This is a division of application Ser. No. 07/244,982, filed Sep. 15, 1988, issued Mar. 5, 1991 as U.S. Pat. No. 4,997,928.

BACKGROUND OF THE INVENTION

1. Field of the Invention

This invention relates to nonnucleoside-containing, fluorescence-tagged, phosphorus reagents, which are useful in the preparation of 5'-tagged oligonucleotides. A class of 5'-fluorescence-tagged oligonuleotides is also disclosed as part of this invention.

2. Summary of the Background

Deoxyribonucleic acid (DNA) is the molecule that stores the information needed to direct all processes in living systems. It is a polymer composed of four mononucleotide subunits linked by phosphodiester bonds. Naturally occurring DNA is usually found in a double-stranded form with two complimentary linear polymers held together by hydrogen bonds. Double-stranded DNA can be dissociated into single strands of DNA and, conversely, complimentary single-stranded DNA will associate to form double-stranded DNA.

Although the terms "DNA" and "oligonucleotide" are often used interchangeably, "DNA" is used herein to refer to large (>100 nucleotides long) or naturally occurring molecules, especially those being subjected to various assays. "Oligonucleotide" is used herein to refer to pieces of single-stranded DNA that are small enough to be made by current, practical chemical synthesis (<100 nucleotides long). The distinction between the terms "DNA" and "oligonucleotide," however, is recognized to be somewhat artificial. DNA can be broken into well-defined pieces that are small enough to be considered as oligonucleotides, and chemically synthesized oligonucleotides can be joined enzymatically to make double-stranded polymers large enough to be called DNA and to direct life processes.

The ability to introduce reporters into oligonucleotides and DNA is, in part, responsible for the recent explosive growth in the field of molecular biology. A reporter can be defined as a chemical group that has a physical or chemical characteristic readily measurable or detectable by appropriate physical or chemical detector systems or procedures. Ready detectability can be provided by such characteristics as color change, luminescence, fluorescence, and radioactivity or it may be provided by the ability of the reporter to serve as a ligand recognition site to form specific ligand-ligand complexes in which the second ligand contains a group detectable by conventional (e.g., colorimetric, spectrophotometric, fluorometric or radioactive) detection procedures. The ligand ligand complexes can be in the form of protein-ligand, enzyme-substrate, antibody-antigen, carbohydrate-lectin, protein-cofactor, protein-effector, nucleic acid-nucleic acid, or nucleic acid-ligand complexes. The complex formed between biotin and avidin is an example of such a ligand-ligand complex.

Although high specific activity $^{32}P$ has generally been used to tag oligonucleotides as well as DNA for a variety of applications, the use of this radioisotope is problematic from both a logistical and a health standpoint. The short half-life of $^{32}P$ necessitates the anticipation of reagent requirements several days in advance and prompt use of such a reagent. Once $^{32}P$-tagged DNA sequencing fragments have been generated, they are prone to self-destruction and must be immediately subjected to electrophoretic analysis. Subsequent autoradiography required for visualization of the labeled DNA fragments on the electrophoretic gel is a slow process (overnight exposures are common). Finally, possible health risks are associated with the use and disposal of such potent radioisotopes.

To address these problems, replacement of $^{32}P$/autoradiography with alternative, nonradioisotopic reporter/detection systems has been considered. New reporter/detection systems must be exceptionally sensitive to replace $^{32}P$ In one sense, DNA can be its own "reporter" because it can be detected by ultraviolet (UV) light absorption. Many important assays, however, require that DNA be detected at concentrations many orders of magnitude below concentrations at which DNA can be detected by UV absorbance. DNA sequencing, for example, requires reporter/detection systems that can detect $10^{-16}$ mole (or about $10^6$ molecules) of DNA. Therefore, practical non-isotopic reporter/detection systems must offer sensitivity at least comparable to that of $^{32}P$ Hereafter, the term "reporter" shall refer only to chemical groups capable of replacing high specific activity $^{32}P$.

Prober, et al., Science 238, 336–41 (1987) and Smith, et al., Nature 321, 674–79 (1986), have shown that, in conjuction with an argon laser and filtered photomultiplier tube detection system, certain fluorescent dyes can replace $^{32}P$ as reporters for DNA sequencing. To achieve the required sensitivity, these dyes were carefully selected for their strong absorption at the wavelength of the argon laser, their high quantum efficiency of fluorescent emission, and the ability to distinguish their fluorescent emission from background signals.

The ability to introduce readily detected reporters at a specific site in DNA is absolutely critical to many methods of analyzing DNA. For example, all currently known methods for sequencing DNA require that several hundred different oligonucleotides be separated by gel electrophoresis. (About $10^{-15}$ to $10^{-16}$ mole of each oligonucleotide is generally present.) Therefore, it is critical that the reporter does not complicate separation by gel electrophoresis. $^{32}P$ is an ideal reporter in this respect because substituting $^{32}P$ for nonradioactive $^{32}P$ has no effect on gel electrophoresis When a nonradioactive reporter, such as a fluorescent dye, is attached to an oligonucleotide, the electrophoretic mobility of that oligonucleotide changes. If only a single reporter is attached to the oligonucleotide at a precisely defined location, such changes are uniform and tolerable. If, however, a variable number of reporters are attached or if a single reporter is attached to a variety of positions, electrophoretic analysis becomes impossible.

DNA amplification by the polymerase chain reaction (PCR) is another technique for analyzing DNA that requires separation by gel electrophoresis. Preferably, oligonucleotides used in this method will also have a non-isotopic reporter at a single location.

Although several methods of non-site-specific enzymatic tagging of DNA are known, only one type of site-specific tagging with non-isotopic reporters is known. The enzyme, terminal transferase, is capable of adding a variety of modified and/or tagged nucleotides to the 3'-end of an oligonucleotide. This enzyme affects single-site tagging only when the 3'-hydroxyl group of the modified and/or tagged nucleotide is removed or changed. Unfortunately, DNA tagged by this method cannot be used in many enzymatic assays. DNA sequencing and amplification, for example, require that the tagged oligonucleotides used in these assays have a normal hydroxyl group at the 3'-end Many chemical methods for tagging DNA have been developed, but most of these involve non-site-specific reactions, thereby producing tagged DNA that is not suitable for analysis by gel electrophoresis. Site-specific tagged oligonucleotides have been prepared by total, i.e., chemical, synthesis. With one exception, this has always been done by synthesizing an oligonucleotide possessing an added group with unusual reactivity, e.g., an aliphatic amino group or a thiol. In this approach, the added amino or thiol groups have either replaced the 5'-hydroxyl group or have been added to the 5'-hydroxyl group by means of a linker or have been added to the base by means of a linker. This site-specific tagging process comprises: (i) preparation of a monomeric nucleotide reagent that contains a protected form of the unusually reactive group; (ii) chemical synthesis and purification of the desired oligonucleotides with the unusually reactive group, usually with concomitant deprotection of the unusually reactive group; and (iii) selective attachment of a fluorescent dye (or other reporter) to the unusually reactive group.

Examples of this and related approaches have been disclosed by Draper, et al., Biochemistry 19, 1774–81 (1980); Smith, DE 3,446,635 Al (1985); Smith, et al., Nucleic Acids Res. 13, 2399–2412 (1985); Coull, et al., Tetrahedron Lett. 27, 3991–94 (1986); Sproat, et al., Nucleic Acids Res. 15, 4837–48 (1987); Sproat, et al., Nucleic Acids Res. 15, 6181–96 (1987); Tanaka, et al., Tetrahedron Lett. 28, 2611–14 (1987); Tanaka, et al., Nucleic Acids Res. 15, 6209–24 (1987); Agrawal, et al., Nucleic Acids Res. 14, 6227–45 (1986); Connolly, Nucleic Acids Res. 15, 3131–39 (1987); Connolly, et al., Nucleic Acids Res. 13, 4485–4502 (1985); and Sinha, et al., Nucleic Acids Res. 16, 2659–69 (1988).

Totally synthetic site-specific tagging approaches present several problems in the synthesis of tagged oligonucleotides.

First, it is a multi-step procedure involving synthesis and purification of a modified oligonucleotide, addition of the reporter to the reactive group of this modified oligonucleotide, and a final purification.

Second, both DNA sequencing and DNA applification require that the tagged oligonucleotide be a substrate for a DNA polymerase. Because these polymerases catalyze ions at the 3'-end of the oligonucleotide, the 5'-end of the oligonucleotide is the preferred site for attaching non-isotopic reporters. When the unusually reactive group is attached to or incorporated within a nucleotide, this approach lacks versatility. The 5'-nucleotide can be dA, dT, dC or dG; therefore, four appropriate reagents are needed for incorporating an unusually reactive group along with the desired 5'-nucleotide. Because these reagents are typically air- and moisture-sensitive and have a limited shelf-life, the need to stock a set of at least four reagents is burdensome.

Third, if a linking group is used to introduce the unusually reactive functional group onto the 5'-position, additional problems arise. It is frequently difficult to determine whether the unusually reactive group has been successfully linked to a synthetic oligonucleotide. Because the reagents used to attach the unusually reactive group to the oligonucleotide have a limited shelf-life, failure to incorporate the desired reporter is common.

Fourth, when problems are encountered, it is usually difficult to determine which step failed.

Fifth, large excesses of the reporter are generally used for successful coupling to the unusually reactive group. This both wastes the reporter and complicates the purification of the oligonucleotide.

In the one exception to the totally synthetic site-specific tagging approaches described above, Prober, et al., EP-A 252,683 (1988), have outlined a more direct and reliable method for synthesizing fluorescence-tagged oligonucleotides for DNA sequencing. An unusually reactive functional group was not used in this approach. Instead, a fluorescent reporter was attached directly to a nucleotide before the nucleotide was incorporated into the desired oligonucleotide.

The principal disadvantage of this method is that it relies on attachment of the reporter to a specific nucleotide and therefore lacks versatility. The resulting fluorescence-tagged oligonucleotide was used in a DNA sequencing system that calls for four distinguishable fluorescent dyes. Complete versatility would require a set of 16 different fluorescence-tagged nucleotide reagents suitable for the synthesis of oligonucleotides. The reagents are also air- and moisture-sensitive and have a limited shelf-life.

The purpose of the present invention is to overcome the problems encountered in the prior art by providing nonnucleoside-containing, fluorescence-tagged, phosphorus reagents to produce 5'-tagged oligonucleotides. The reagents disclosed in the present invention are easier to prepare and are more versatile than are the compounds found in Prober, et al., EP-A 252,683. The presence of the reporters of the present invention in the resulting oligonucleotides does not interfere with analysis by gel electrophoresis or with use in DNA sequencing or DNA amplificaton. Fewer steps are required and the chances for error or confusion have been reduced when these reporters are used.

The 5'-tagged oligonucleotides of the present invention can be used as labeled primers for automated DNA sequencing and for DNA amplification by the polymerase chain reaction (PCR).

SUMMARY OF THE INVENTION

The present invention provides chemical reagents of the formula reporter—A—Q wherein the reporter is selected from the group consisting of protected fluorescent reporters and unprotected fluorescent reporters; A is selected from the group consisting of $$-O-, -S-, -\underset{|}{N}R, \text{ and } -\underset{|}{C}RR^1,$$

wherein R and $R^1$ are independently selected from the group consisting of H, $C_3$-$C_{10}$ branched alkyl, $C_1$-$C_{10}$ unbranched alkyl, $C_6$-$C_{10}$ aryl, $C_7$-$C_{12}$ alkaryl, and $C_7$-$C_{12}$ aralkyl; and Q is selected from the group consisting of and salts thereof, wherein $R^2$ and $R^3$ are independently selected from the group consisting of $C_3$–$C_{10}$ branched alkyl and $C_1$–$C_{10}$ unbranched alkyl; $R^4$ is selected from the group consisting of —$(CRR^1)_m(A)_n(CRR^1)$—, wherein R, $R^1$, and A are as defined above, $m=1-6$, $n=0-1$, $p=1-10$, and $q=0-10$, provided that $2m+n \leq 12$ and further provided that $2 \leq n+p+q \leq 13$; X is selected from the group consisting of F, —Cl, —Br, —I, imidazol-1-yl, 1,2,4-triazol-1-yl, tetrazol-1-yl, and 1-hydroxybenzotriazol-0-yl; and Y is any phosphate-protecting group.

Additionally, the present invention includes a class of 5'-fluorescence-tagged oligonucleotides. These oligonucleotides are conveniently prepared using the reagents of the present invention. The general structure of this class of oligonucleotides is

DETAILED DESCRIPTION OF THE INVENTION

Nonnucleoside-containing, fluorescence-tagged phosphorus reagents of the present invention are useful in the preparation of 5'-tagged oligonucleotides. These reagents are of the formula reporter—A—Q wherein the reporter is selected from the group consisting of protected fluorescent reporters and unprotected fluorescent reporters; A is selected from the group consisting of wherein $R^5$ and $R^6$ are independently selected from the group consisting of —H, $C_1$–$C_4$ alkyl, —F, —Cl, —Br, —I, $C_1$–$C_4$ alkoxy, and —CN; B is selected from the group consisting of 1-thyminyl, 1-cytosinyl, 1-uracilyl, 9-adeninyl, and 9-guaninyl; $R^9$ is selected from the group consisting of —H and —OH; and $n=0$ to about 100.

$-O-$, $-S-$, $-NR$, and $-CRR^1$, wherein R and $R^1$ are independently selected from the group consisting of H, $C_3$–$C_{10}$ branched alkyl, $C_1$–$C_{10}$ unbranched alkyl, $C_6$–$C_{10}$ aryl, $C_7$–$C_{12}$ alkaryl, and $C_7$–$C_{12}$ aralkyl; and Q is selected from the group consisting of and salts thereof, wherein $R^2$ and $R^3$ are independently selected from the group consisting of $C_3$-$C_{10}$ branched alkyl and $C_1$-$C_{10}$ unbranched alkyl; $R^4$ is selected from the group consisting of —$(CRR^1)_m(A)_n(CRR^1)_m$—, wherein R, $R^1$, and A are as defined above, m = 1-6, n = 0-1, p = 1-10, and q = 0-10, provided that $2m+n \leq 12$ and further provided that $2 \leq n+p+q \leq 13$; X is selected from the group consisting of —F, —Cl, —Br, —I, imidazol-1-yl, 1,2,4-triazol-1-yl, tetrazol-1-yl, and 1-hydroxybenzotriazol-O-yl; and Y is any phosphate-protecting group. The reporter is covalently linked to the activatable phosphorus group, Q.

Preferably, A is —O—, in which case these reagents are commonly known (with reference to the activatable phosphorus group, Q) as phosphoramidites (1 and 2), phosphorous acids (3), H-phosphonates (4), and activated phosphodiesters (5). Structures (3) and (4) represent moderately strong acids, and the reagents represented by these structures are generally isolated and used as their organically soluble salts.

The H-phosphonate forms (4) of these reagents are generally in equilibrium with the phosphorous acid forms (3), with the H-phosphonates strongly favored. Analogous equilibria are established when The phosphorus group, Q, includes Y, which can be any phosphate-protecting group. Preferably, Y is selected from the group consisting of 4—Cl—$C_6H_4$—O—, 2—Cl—$C_6H_4$—O—, 4—$NO_2$—$C_6H_4$—O—, 4—$NO_2$—$C_6H_4CH_2CH_2$—O—, 2,4—$NO_2$—$C_6H_3CH_2CH_2$—O—, 2,4—$Cl_2$—$C_6H_3$—O—, 2,3—$Cl_2$—$C_6H_3$—O—, $NCCH_2CH_2O$—, $NCCH_2C(CH_3)_2$—O—, $CH_3O$—, $(Z)_3CCH_2$—O—, $(Z)_3CC(CH)_2$—O—, R'S—, $R'SCH_2CH_2$—O—, $R'SO_2Ch_2CH_2$—O—, and R'NH—, wherein Z is selected from the group consisting of Cl, Br, and I, and R' is selected from the group consisting of H, $C_3$-$C_{10}$ branched alkyl, $C_{1-10}$ unbranched alkyl, $C_6$-$C_{10}$ aryl, $C_7$-$C_{12}$ alkaryl, and $C_7$-$C_{12}$ aralkyl. The most preferred Y groups are $NCCH_2CH_2O$—, $CH_3O$—, and 2-Cl-$C_6H_4$—O—.

A suitable fluorescent reporter is one that can be detected in its unprotected form at or below the level of detection that can be quickly achieved with $^{32}P$, i e., about $10^{-14}$ moles. Specific desirable characteristics may include a large coefficient of extinction in the region of excitation, a high quantum yield, an optimal excitation or emission wavelength (preferably above 350 nm), and photostability. For example, fluorescent dyes that are efficiently excited by an argon laser are desirable because of the low cost of this laser.

Preferably, in its unprotected form, the reporter is a fluorescent dye chosen from the group consisting of xanthenes (e.g., fluoresceins, eosins, erythrosins), rhodamines (e.g., tetramethylrhodamine, Texas Red ®), benzamidizoles, ethidiums, propidiums, anthracyclines, mithramycins, acridines, actinomycins, merocyanines, coumarins (e.g., 4-methyl-7-methoxycoumarin), pyrenes, chrysenes, stilbenes, anthracenes, naphthalenes (e.g., dansyl, 5-dimethylamino-1-naphthalenesulfonyl), salicylic acids, benz-2-oxa-1-diazoles (also known as benzofurazans) (e.g., 4-amino-7-nitrobenz-2-oxa-1,3-diazole), and fluorescamine. Useful forms of many of these dyes are commercially available. For a review of fluorescent dyes used in tagging DNA, see A. S. Waggoner, Chapter 1, Applications of Fluorescence in the Biomedical Sciences, ed. by D. L. Taylor, et al., Alan R. Liss, New York (1986).

Most preferably, the reporter is a xanthene, especially a xanthene represented by the structure wherein $R^5$ and $R^6$ are independently selected from the group consisting of —H, $C_1$-$C_4$ alkyl, —F, —Cl, —Br, —I, $C_1$-$C_4$ alkoxy, and —CN; $R^7$ is $C_1$-$C_4$ alkyl; and $R^8$ is selected from the group consisting of alkyl or aryl.

Using methods known in the art, a covalent link can be made between these dyes and the activatable phosphorus group, Q. For reasons of synthetic ease and stability, Q is usually attached to an oxygen, which was formerly part of a hydroxyl group in the reporter. In some cases, the activatable phosphorus group, Q, can be attached directly to the fluorescent dye at a site that does not interfere with its utility as a reporter. In other cases, a covalent linkage can be formed by selectively attaching one of these dyes to one end of a small, difunctional molecule and the activatable phosphorus to the other end of this molecule. Most of the fluorescent reporters listed above are available commercially in a form suitable for attachment to a small, difunctional molecule.

In some cases, it may be necessary to protect sensitive functional groups on the reporter during the attachment of the activatable phosphorus group, activation of the phosphorus group, or attachment of the phosphorus group to the 5'-hydroxyl group of the oligonucleotide. The nature of the protecting group(s), if present, will depend on the sensitive functional groups on the reporter. The preferred xanthene dyes of this invention have nucleophilic hydroxyl groups that need protection. Methods for protecting and deprotecting a wide variety of functional groups are known in the art and have been reviewed in J. F. W. McOmie (ed.), Protective Groups in Organic Chemistry, Plenum Press, New York (1973).

Because automated DNA synthesizers generally use the phosphoramidite approach to oligonucleotide synthesis, the preferred phosphorus reagents of this invention are phosphoramidites, i.e., when A is -O- and Q is selected from the group consisting of

(1)

(2)

employed with xanthene dyes, preferably of the structure specified above. A preferred embodiment is wherein $R^2$ and $R^3$ of the activatable phosphorus group, Q, are —CH(CH$_3$)$_2$.

The reagents discussed above are useful in the preparation of 5'-fluorescence-tagged oligonucleotides. Appropriate processes for using these reagents to form a covalent bond between the activatable phosphorus group, Q, and the 5'-hydroxyl group of an oligonucleotide are known. These processes can be combined with other known methods of synthesizing oligonucleotides to prepare 5'-fluorescencetagged oligonucleotides. For a general review of the field of oligonucleotide synthesis, see M. J. Gait (ed.), Oligonucleotide Synthesis, A Practical Approach, IRL Press, Oxford (1984). In cases wherein the fluorescent reporter is used in a protected form, an additional deprotection step may be required.

In addition to the disclosed reagents, the present invention includes a class of 5'-fluorescence-tagged oligonucleotides. These oligonucleotides are conveniently prepared using the reagents of the present invention and processes known in the art of oligonucleotide synthesis. The general structure of this class of oligonucleotides is wherein $R^5$ and $R^6$ are independently selected from the group consisting of —H, $C_1$-$C_4$ alkyl, —F, —Cl, —Br, —I, $C_1$-$C_4$ alkoxy, and —CN; B is selected from the group consisting of 1-thyminyl, 1-cytosinyl, 1-uracilyl, 9-adeninyl, and 9-guaninyl; $R^9$ is selected from the group consisting of —H and —OH; and n=0 to about 100.

These oligonucleotides can be used in automated fluorescence-based DNA sequencing, according to the methods described in Prober, et al., Science 238, 336–41 (1987) and Ansorge, et al., J. Biochem. Biophys. Methods, 13, 315-23 (1986). Additionally, they can be used in DNA amplification by the polymerase chain reaction (PCR) method, according to the methods described in U.S. Pat. Nos. 4,683,195 and 4,683,202.

EXAMPLES

General Procedure

The following Examples illustrate, but do not limit, the compounds and utilities of the present invention. Examples 1–4 demonstrate the preparation of the claimed reagents; Examples 5 and 6 disclose the claimed class of 5'-fluorescence-tagged oligonucleotides and describe a process by which they can be produced; and Examples 7 and 8 refer to the utility of these reagents and 5'-fluorescence-tagged oligonucleotides.

The following diagram is referred to in the Examples. Structures 7a-d, 8a-d, and 9a-d are protected forms of the preferred xanthene reporters. The activatable phosphorus group, Q, which is P(OCH$_2$CH$_2$CN)(N(i-Pr)$_2$) in the diagram, is added to the reporter between 8 and 9. The last structure summarizes the fluorescent-tagged oligonucleotides of the present invention.

7a-d 8a-d 9a-d a: $R^5 = R^6 = H$.   b: $R^5 = H, R^6 = CH_3$.   c: $R^5 = CH_3, R^6 = H$.   d: $R^5 = R^6 = CH_3$.
xxx = 505.   xxx = 512.   xxx = 519.   xxx = 526.

All temperatures are in degrees Celsius (25° C refers to ambient or room temperature). All parts and percentages not otherwise indicated are by weight except for mixtures of liquids, which are by volume. The following abbreviations are employed: DMF for dimethylformamide; DMSO for dimethylsulfoxide; SF for succinylfluorescein; NMR for nuclear magnetic resonance spectrum; IR for infrared spectrum; UV for ultraviolet spectrum or detection; TLC for thin layer chromatography on silica gel; HPLC for high pressure liquid chromatogrphy; GC for gas chromatography; mp for melting point; mp d for melting point with decomposition; and bp for boiling point. In reporting NMR data, chemical shifts are given in ppm and coupling constants (J) are given in Hertz. All melting points are uncorrected. Ion exchange resins were washed with appropriate aqueous and organic solvents prior to use. The identity of all compounds described herein was established by appropriate spectroscopic and ananlytical techniques. Unless other noted, purification by chromatography on silica gel was performed as described by Still, et al., J. Org. Chem. 43, 2923–26 (1978).

EXAMPLE 1

Preparation of Phosphoramidite 9a

Step 1: Preparation of N-(3-(3,6-diacetoxy-9-ethoxy-9H-xanthen9-yl)propionyl)-4-hyroxypiperidine, 8a.

A solution of 4-hydroxypiperidine (506 mg, 5.00 mmol, 2.5 eq, Aldrich) and 9-(2-(N-succinimidyloxycarbonyl))ethyl)-3,6-diacetoxy-9-ethoxy-9H-xanthene, 7a (1.023 g, 2.00 mmol, prepared according to Prober, et al., EP-A 252,683) in dry dichloromethane (20 ml) was stirred for 30 min. The reaction was added to 1M aqueous potassium phosphate buffer (30 mL; pH =7) and extracted with dichloromethane (3×30 mL). The organic extracts were dried over calcium sulfate, concentrated, and dried under vacuum overnight to afford crude amide 8a (1.039 g, 104%) as an off-white foam. This material was >90% pure according to NMR and TLC and was used without further purification in the next step.

$^1$H-NMR (DMSO-d$_6$): 7.58 (m, 2H, ArH0, 7.04 (m, 4H, ArH), 4.66 (d, J=4, 1H, OH), 3.72 (br m, 1H, NCH$_2^1$), 3.57 (app octet, 1H, CHOH), 3.17 (br m, 1H, NCH$_2^b$), 2.88 (q, J=7, 2H, OCH$_2$CH$_3$), 2.83 (m, 2H, NCH$_2^c$ and CH$_2^d$), 2.29 (s, 6H, OAc), 2.22 (app dist t, J=8, 2H, CH$_2$CO), 1.73 (app dist dd, 2H, CH$_2$Ar), 1.58 (m, 2H, CH$_2^1$CHOH), 1.11 (m, 2H, CH$_2^b$CHOH), and 1.03 (t, J=7, 3H, OCH$_2$CH$_3$). TLC (9:1 dichloromethane-methanol); UV): starting material 7, R$_f$=0.87; amide product 8a, 0.49.

Step 2: Preparation of 2-cyanoethyl (N-(b 3-(3,6-diacetoxy-9-ethoxy-9H-xanthen-9-yl)propionyl) piperidin-4-yl)oxy N,N-diisopropyl phosphoramidite, 9a.

Crude amide 8a (1.00 g, ca. 1.98 mmol) was coevaporated with dry pyridine (1×10 mL) and dry toluene (2×10 mL) and then vacuum dried. Dry dichloromethane (15 mL), dry diisopropylamine (0.14 mL, 1.00 mmol, 0.5 eq), tetrazole (70.0 mg, 1.00 mmol, 0.5 eq, Aldrich Gold Label), and 2-cyanoethyl N,N,N',N'-tetraisopropylphosphorodiamidite (0.76 mL, 2.41 mmol, 1.2 eq, Aldrich) were added sequentially. After stirring the resulting solution for 2 hours, the reaction mixture was added to 30 mL of 1M aqueous potassium phosphate buffer (30 mL, pH =7) and extracted with ether (3×30 mL). The ether extracts were dried over calcium sulfate and concentrated. The residue was chromatographed on silica gel (100 g) with a 70:28:2 mixture of dichloromethane, ethyl acetate and pyridine. The first UV absorbing component to elute was concentrated, coevaporated with dry toluene. (2×30 mL), and vacuum dried to afford phosphoramidite 9a, (893 mg, 65%). Except for the presence of residual toluene (16 mole%), this material was >95% pure by $^1$H and $^{31}$P-NMR and TLC. According to $^{31}$P-NMR, this material was stable in dry DMSO-d$_6$ in a normally sealed NMR tube for at least a week at room temperature.

$^1$H-Decoupled $^{31}$P-NMR (DMSO-d$_6$): 146.8 (s). $^{11}$P-Coupled H-NMR (DMSO-d$_6$): 7.58 (d, 2H, ArH), 7.23 (m, 0.32H, toluene), 7.18 (m, 0.48H, toluene), 7.04 (m, 4H, ArH), 3.94 (m, 1H, CHOP), 3.68 (m, 2H, CH$_2$OP), 3.57 (m, 2H, NCH), 3.49 (br m, 1H, NCH$_2^a$), 3.18 (br m, 2H, NCH$_2^b$ and NCH$_2^c$), 2.96 (br m, 1 H, NCH$_2^d$), 2.88 (q, J=7, 2H, OCH$_2$CH$_3$), 2.74 (t, J=6, 2H, CH$_2$CN), 2.31 (s, 0.48 H, toluene), 2.30 (s, 6H, OAc), 2.23 (app dist t, J=8, 2H, CH CO), 1.57 (app dist dd, 2H, ArCH:), 1.63 (br m, 2H, CH$_2^a$COP), 1.37 (br m, 2H, CH$_2^b$), 1.13 (app dist t, 12H, CH(CH$_3$)$_2$), and 1.03 (t, J=7, 3H, OCH$_2$CH$_3$).

EXAMPLES 2–4

Preparation of Phosphoramidites 9b-9d

Phosphoramidites 9b-9d were prepared from N-hydroxysuccinimidyl esters 7b-7d as described for phosphoramidite 9a in Example 1. The final phosphoramidites were purified on silica gel in the presence of pyridine. Pyridine (4%) in toluene was found to be the preferred eluent. Chromatography fractions were preferably analyzed by TLC on silica gel plates that had been deactivated by treatment with 5% pyridine in pentane. Fractions containing pure phosphoramidite were combined, coevaporated with dry pyridine (4×10 mL) and dry toluene (2×10 mL), and vacuum dried.

$^1$H-Decoupled $^{32}$P-NMR (DMSO-d$_6$):
9b 147.0 (s) and 146.9 (s).
9c 146.9 (s)
9d 147.0 (s) and 146.9 (s).

In the cases where two phosphorus signals were observed by NMR, the two signals coalesced to a single signal upon warming to 70°. (The NMR spectra of all of the above compounds were best explained by variable restricted rotation about the amide bond.)

EXAMPLE 5

Preparation of SF505-4HP-pGTTTTCCCAGTCACGAC, An Oligonucleotide with the Fluorescent Reporter SF505-4HP-p Attached to the 5'-Oxygen Automated oligonucleotide synthesis was performed on a Du Pont Code ® 300 according to the general methods described in the operator's manual. The sequence "5'-XGTTTTCCCAGTCACGAC 3'" was entered and the following options were selected: (1) Use capping step? YES. (2) Remove 5' terminal DMT? NO. (3) Collect DMT? YES. (4) Synthesis scale 1 μmole. The instrument was charged with reagents supplied commercially by Du Pont and an 0.1 M solution of phosphoramidite 9a in dry acetonitrile was placed on the "X" port using a manual line purge (3×50 μL) instead of the automated bottle change function. The starting material in the synthesis column was N-anisoyl-5'-dimethoxy-trityl-2'-deoxycytidine (1 μmol) on long chain alkylamine controlled pore glass. Automated synthesis was run without any modification during or after the use of phosphoramidite 9a. Analysis of the dimethoxytrityl cation released indicated that the overall yield of untagged 17-mer on the solid support was 75% before phosphoramidite 9a was used. (The average coupling efficiency per cycle therefore was 98.3%.) After automated synthesis was complete, the solid support was removed from the synthesis column and stirred for 1 hour with concentrated ammonium hydroxide (4 mL). The solid support was removed by filtration through a plug of glass wool into a vial and the vial was topped off with additional concentrated ammonium hydroxide (approximately 1 mL). The vial was tightly sealed and heated at 55° for 4 hours. (Longer deprotection can cause production of a significant amount of nonfluorescent oligonucleotide side product.) After cooling, the ammonia solution was concentrated under vacuum.

The deep orange residue was dissolved in water (1000 μL). An aliquot (10 μL) of this solution and 0.05 M aqueous Tris buffer (990 μL, pH 8.2) were placed in a 1 cm pathlength UV cell. The absorbance was 0.813 and 0.186 at the maxima at 260 and 493 nm respectively, indicating that the crude product amounted to 81.3 ODU (260 nm) or 18.6 ODU (493 nm). Assuming the absorption coefficient of the chromophore (72,600 at 493 nm and 23,000 at 260 nm; see Prober, et al., Science 238, 336–41 (1987)) is unchanged by attachment to an oligonucleotide, the yield of crude fluorescent oligonucleotide was 25%. Analysis of the crude product by HPLC (20 cm C8 reverse phase column eluted at 1 mL/min for 25 minutes with a gradient of 0–25% acetonitrile in 0.1M aqueous triethylammonium acetate) with detection at 260 nm and 500 nm showed that the largest peak at 260 nm was the only significant product (>90%) absorbing at 500 nm.

The remainder of the crude product was purified by preparative HPLC on a 300 A° C8 Dynamax ® column (1×25 cm). The column was eluted with a 5–20% gradient of acetonitrile in 0.1M aqueous triethylammonium acetate over 35 minutes with a flow rate of 5 mL/min. The major peak (22 minutes) was collected and dried under vacuum. The purified oligonucleotide was dissolved in water and assayed by UV as before. The yield was 38.6; 10DU (260 nm) and 15.2 ODU (493 nm). Assuming the absorption coefficient of the oligonucleotide product is the sum of the absorption coefficients of its subunits (192,000 at 260 nm), the yield of purified product was 20%. The ratio of the absorbances observed at 493 and 260 (2.54:1) for the purified product was within experimental error of theoretical ratio (2.64:1) calculated for a product containing one SF505 chromophore per oligonucleotide. The product was lyophilized, dissolved in sterile distilled water, and stored frozen at −25° until used.

EXAMPLE 6

Preparation of Other Fluorescently Tagged Oligonucleotides

Following the procedures of Example 5, SF512-4HP-p-, SF519-4HP-p-, and SF526-4HP-pgroups were attached to the 5'-end of the same oligonucleotide with phosphoramidites 9b–9d. The UV maxima of the products were 500, 511, and 518 nm respectively.

Subsequently, following the procedures of Example 5, succinylfluorescein dyes were attached to oligonucleotides with different sequences of bases.

EXAMPLE 7

DNA Suquencing with an SF505-4HP-p-Tagged Primer Using a Modified Sanger Chain Elongation Protocol The following components were mixed in each of four 1.5 μL Eppendorf tubes: 12 μL M13 mp18 single-stranded DNA template (N. E. BioLabs; 0.25 μg/μL), 3 μL SF505-4HP-pGTTTTCCCAGTCACGAC primer solution (Example 5; 0.30 ODU (260 nm)/μL=1.5 μM), 3 μL 10X Taq polymerase reaction buffer (166 mM $(NH_4)_2SO_4$; 670 mM Tris-HCl, pH 8.8; 67 mM $MgCl_2$; 100 mM b-mercaptoethanol; 67 μM EDTA; 1.7 mg/mL bovine serum albumin), and 5 μL $H_2O$. Each tube was heated for two minutes in a boiling water bath, then allowed to cool to room temperature over a 15-minute period. Five μL of a nucleotide solution were added to the four tubes; one tube receiving the ddA mix, another the ddC mix, another the ddG mix, and another the ddT mix. These mixes contain the following concentrations of dideoxy- and deoxynucleotide triphosphates:

|       | ddA Mix | ddC Mix | ddG Mix | ddT Mix |
|-------|---------|---------|---------|---------|
| ddATP | 300 mM  | —       | —       | —       |
| ddCTP | —       | 100 m   | —       | —       |
| ddGTP | —       | —       | 150 mM  | —       |
| ddTTP | —       | —       | —       | 500 mM  |
| dATP  | 25 mM   | 250 mM  | 250 mM  | 250 mM  |
| dCTP  | 250 mM  | 25 mM   | 250 mM  | 250 mM  |
| dGTP  | 250 mM  | 250 mM  | 25 mM   | 250 mM  |
| dTTP  | 250 mM  | 250 mM  | 250 mM  | 25 mM   |

Reactions were initiated by adding 1 μL 40 mM dithiothreitol and 1 μL Taq DNA polymerase (Cetus; 5 units/μL) to each tube. The reactions were incubated at 65° for 30 minutes. Each reaction was passed through a G-50 Select-D spin column (5 Prime+3 Prime, Inc.; Paoli, PA), which had been prewashed with $H_2O$. Each column effluent was collected and vacuum dried. Each pellet was resuspended in 5 μL 95% (v/v) formamide and incubated at 68° for ten minutes. Three μL of each sample were loaded on an 8% polyacrylamide-8 M urea sequencing gel and analyzed on the Genesis®2000 DNA Analysis System (Du Pont) following the manufacturer's instructions.

Figure 1:
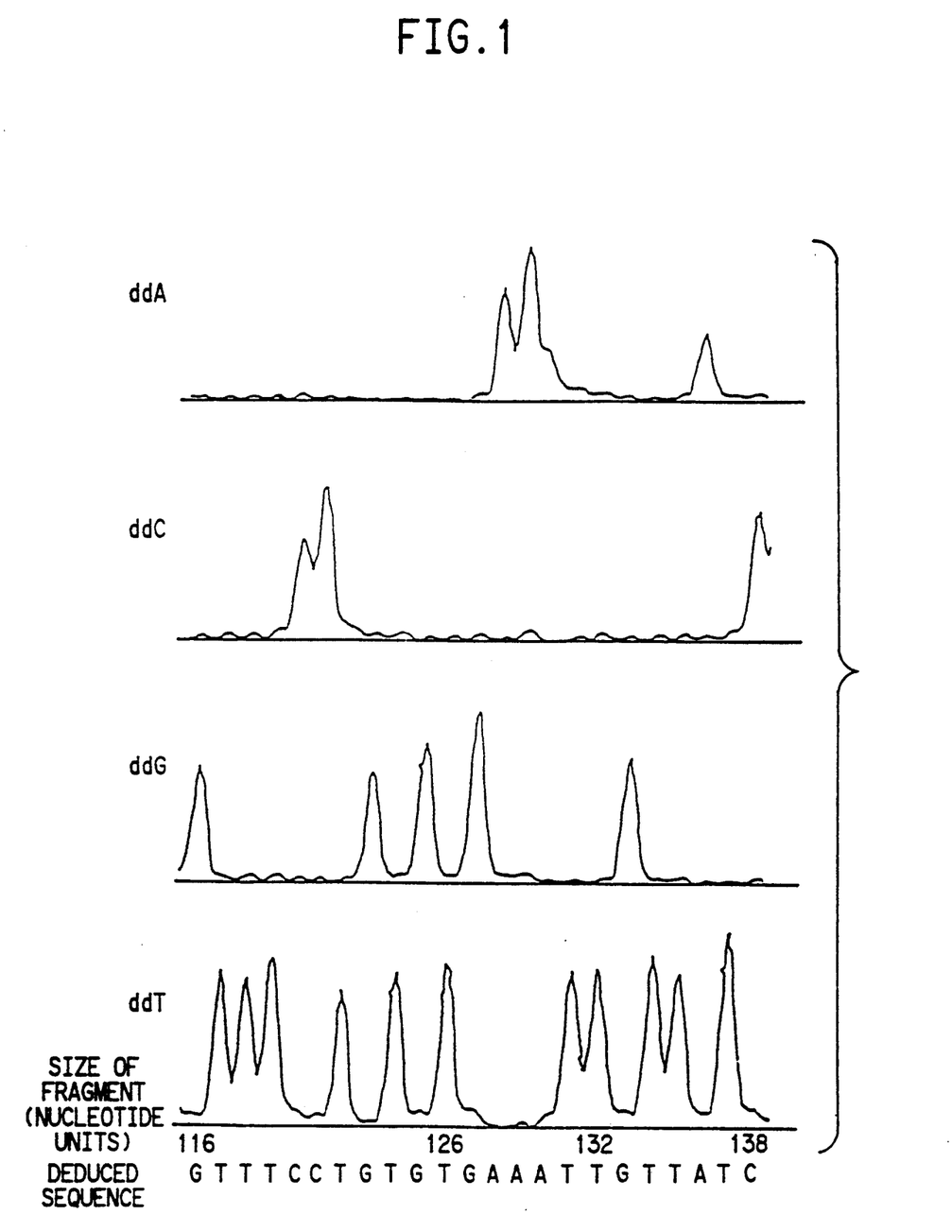
FIG. 1 shows a plot of fluorescent emission against time observed during electrophoresis for the four samples prepared in Example 7. The figure demonstrates that primer extension products derived from 5'-fluorescence tagged oligonucleotides can be detected by their fluorescent emission. The figure also demonstrates that the sequence of bases in the DNA template can be deduced from this plot.

A portion of the fluorescent emission detected during electrophoresis of the four samples of this example is shown in FIG. 1. The pattern of chain terminations allows the sequence of a portion of M13 mp18 to be accurately deduced. This demonstrates (i) that the presence of the SF505-4HP moeity did not interfere with the ability of the primer to hybridize with the DNA template, (ii) that the SF505-4HP primer is a substrate that can be extended by a DNA polymerase, and (iii) that the primer products can be detected by their characteristic fluoresence.

EXAMPLE 8

Polymerase Chain Reaction with an SF505-4HP-p-Tagged Primer

An SF505-4HP-pGTTTTCCCAGTCACGAC primer (Example 5) was used as part of a polymerase chain reaction, which is a process for amplifying specific segments of DNA and is described in detail in U.S. Pat. Nos. 4,683,195 and 4,683,202. The sequence to be amplified was a 337 base pair segment of M13 mp18. The second primer used in the polymerase chain reaction was an unlabeled 17-mer oligodeoxynucleotide with the sequence AAACCACCCTGGCGCCC (5'→3') prepared by standard automated procedures. The following components were mixed: 62 μL H$_2$O, 10 μL 10X Taq polymerase reaction buffer (166 mM (NH$_4$) SO$_4$; 670 mM Tris-HCl, pH 8.8; 67 mM MgCl$_2$; 100 mM β-mercaptoethanol; 67 μM EDTA; 1.7 mg/mL bovine serum albumin), 16 μL deoxynucleotide triphosphate solution (1.25 mM dATP; 1.25 mM dCTP; 1.25 mM dGTP; 1.25 mM dTTP), 5 μL SF505-4HP-pGTTTTCCCAGTCACGAC primer solution (Example 5; 0.30 ODU (260 nmol)/μL =1.5 μM), 5μL AAACCACCCTGGCGCCC primer solution (0.30 ODU (260 nm)/mL=1.8 μM)), 1 μL M13 mp18 single-stranded DNA (N. E. BioLabs, diluted to a concentration of 1 ng/μL), and 1 μL Taq DNA polymerase (Cetus; 5 units/μL).

This reaction mixture was heated to 94° for one minute, cooled to 45° and incubated for two minutes, then heated to 72° and incubated for three minutes. This temperature cycle was repeated an additional 24 times. The DNA in the reaction was precipitated by adding 100 μL 5 M ammonium acetate plus 500 μL ethanol. The precipitated DNA was collect by centrifugation, dried under vacuum, resuspended in 100 μL 95% (v/v) formamide, and incubated at 68° for 10 minutes. One μL of this sample was loaded on an 8% polyacrylamide-8 M urea sequencing gel and analyzed on the Genesis ® 2000 DNA Analysis System (Du Pont) following the manufacturer,s instructions.

Figure 2:
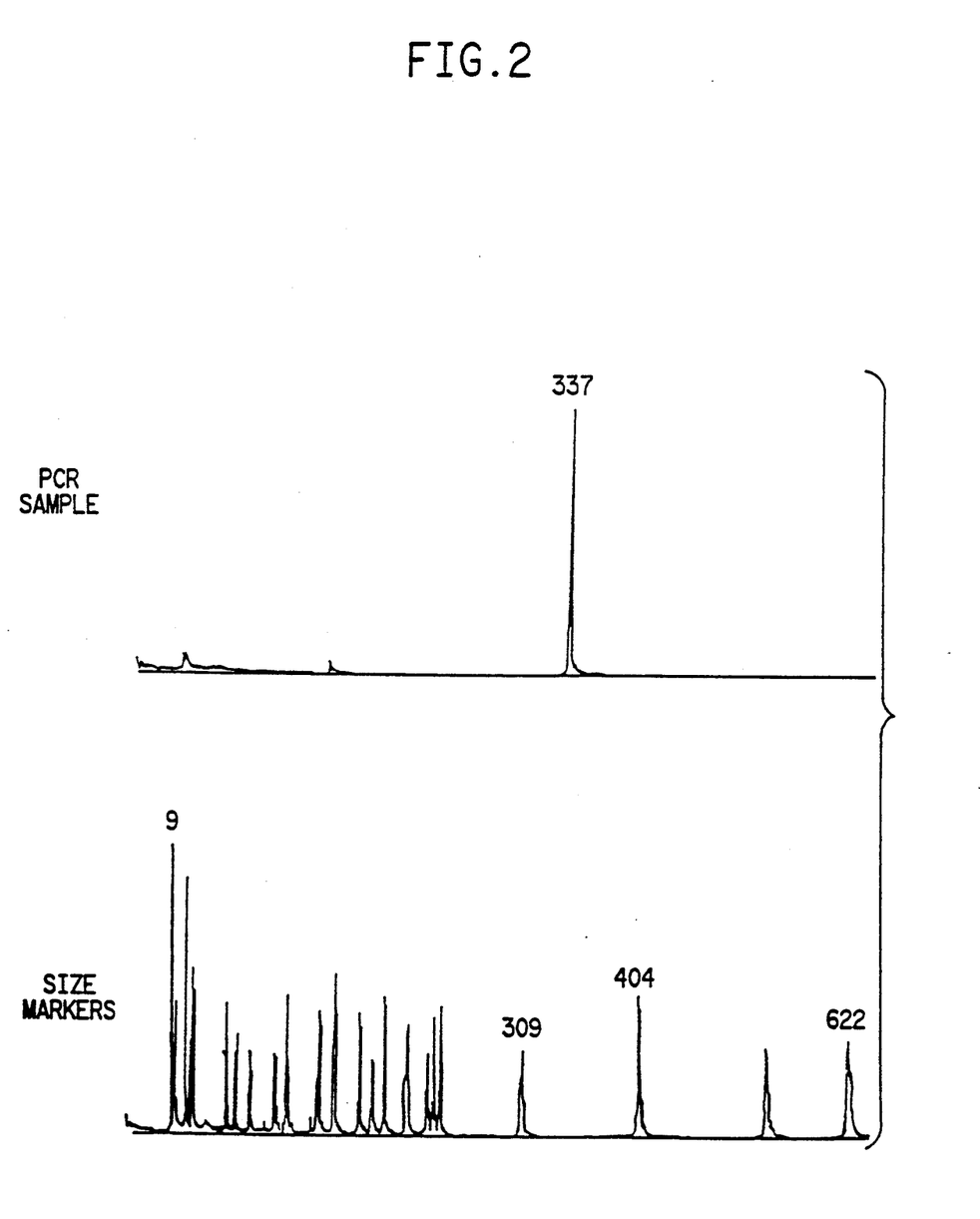
FIG. 2 shows a plot of fluorescent emission against time observed during electrophoresis of the amplified sample of DNA produced in Example 8 and a similar plot of size markers. This figure demonstrates that amplification products derived from 5'-fluorescence-tagged oligonucleotide primers can be detected by their fluorescent emission. The figure also demonstrates that the major product of the amplification process is, as expected, a fluorescence-tagged oligonucleotide of approximately 337 base pairs in size.

Fluorescent emissions detected during electrophoresis of the polymerase chain reaction products are shown in FIG. 2. Also shown are size markers that consist of labeled restriction fragments electrophoresed in a parallel lane. The size markers are pBR322 MspI restriction fragments (N. E. BioLabs) end-labeled with SF519-ddCTP (New England Nuclear) by standard procedures. FIG. 2 shows that the major product of the polymerase chain reaction is, as expected, a DNA fragment approximately 337 base pairs in size. This demonstrates (i) that the presence of a 5'-SF505-4HP moeity does not interfere with the use of an oligodeoxynucleotide in the polymerase chain reaction and (ii) the products of the polymerase chain reaction can be detected by their characteristic fluorescence.

What is claimed is:

1. A nonnucleoside-containing chemical reagent having the formula

Q—O—reporter wherein Q is a phosphorus group suitable for attachment to the 5'-hydroxyl group of an oligonucleotide selected from the group of phosphorus groups consisting of and salts thereof;

wherein R$^2$ and R$^3$ are independently selected from the group consisting of C$_3$-C$_{10}$ branched alkyl and C$_1$-C$_{10}$ unbranched alkyl;

wherein R$^4$ is selected from the group consisting of —(CRR$^1$)$_m$(A)$_n$(CRR$^1$)$_m$—, wherein A is selected from the group consisting of wherein R and R$^1$ are independently selected from the group consisting of H, C$_3$-C$_{10}$ branched alkyl, C$_1$-C$_{10}$ unbranched alkyl, C$_6$-C$_{10}$ aryl, C$_7$-C$_{12}$ alkaryl, and C$_7$-C$_{12}$ aralkyl;

wherein m=1-6, n=0-1, p=1-10, and q=0-10, provided that 2m+n≦12 and further provided that 2≦n+p+q ≦13;

wherein X is selected from the group consisting of —F, —Cl, —Br, —I, imidazol-1-yl, 1,2,4-triazol-1yl, and 1-hydroxybenzotriazol-O-yl;

wherein Y is selected from the group consisting of 4-Cl-C$_6$H$_4$-O-, 2—Cl—C$_6$H$_4$—O—, 4—NO$_2$—C$_6$H$_4$—O—, 4NO$_2$—C$_6$H$_4$CH$_2$CH$_2$—O—, 2,4—NO$_2$—C$_6$H$_3$CH$_2$CH$_2$—O—, 2,4-Cl$_2$—C$_6$H$_3$—O—, 2,3—Cl$_2$—C$_6$H$_3$—O—, NCCH$_2$CH$_2$O—, NCCH$_2$C(CH$_3$)$_2$—O—, CH$_3$O—, (Z)$_3$CCH$_2$—O—, (Z)$_3$CC(CH$_3$)$_2$—O—, R'S—, R'SCH$_2$CH$_2$—O—, R'SO$_2$CH$_2$CH$_2$—O—, and R'NH—;

wherein Z is selected from the group consisting of Cl, Br, and I;

wherein R' is selected from the group consisting of H, C$_3$-C$_{10}$ branched alkyl, C$_1$-C$_{10}$ unbranched alkyl, C$_6$-C$_{10}$ aryl, C$_7$-C$_{12}$ alkaryl, and C$_7$-C$_{12}$ aralkyl;

wherein the —O— in —O—reporter was formerly part of a hydroxyl group and is covalently linked to said Q; and wherein the —O—reporter is either (i) a fluorescent reporter selected from the group of fluorescent dyes consisting of fluoresceins, benzamidizoles, ethidium,s propidiums, anthracyclines, mithramycins, actinomycins, merocyanines, coumarins, pyrenes, chrysenes, stilbenes, anthracenes, naphtha- lenes, salicylic acids, benz-2-oxadiazoles, and fluorescamine, or (ii) a protected from of one of said fluorescent reporters.

2. A compound according to claim 1 wherein $R^4$ is selected from —$(CRR^1)_m(A)_n(CRR^1)m$—, and 3. A compound according ot claim 1 wherein Y is selected from the group consisting of $NCCH_2CH_2O$—, $CH_3O$—, and 2-Cl-$C_6H_4$—O—.

4. A compound according to claim 1 or claim 3 wherein Q is selected from the group consisting of 5. A compoudn according to claim 4 wherein the reporter is a fluorescein.

6. A compound according to claim 4 wherein the reporter is a coumarin.

* * * * *